(12) United States Patent
Yang et al.

(10) Patent No.: US 11,806,551 B2
(45) Date of Patent: Nov. 7, 2023

(54) DOSIMETRIC FEATURES-DRIVEN MACHINE LEARNING MODEL FOR DVHS/DOSE PREDICTION

(71) Applicant: The Board of Trustees of the Leland Stanford Junior University, Stanford, CA (US)

(72) Inventors: Yong Yang, Cupertino, CA (US); Lei Xing, Palo Alto, CA (US); Ming Ma, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 684 days.

(21) Appl. No.: 16/697,725

(22) Filed: Nov. 27, 2019

(65) Prior Publication Data
US 2020/0171325 A1 Jun. 4, 2020

Related U.S. Application Data

(60) Provisional application No. 62/772,802, filed on Nov. 29, 2018.

(51) Int. Cl.
*G06N 20/10* (2019.01)
*A61N 5/10* (2006.01)
*G06F 17/18* (2006.01)

(52) U.S. Cl.
CPC ........... *A61N 5/1031* (2013.01); *G06F 17/18* (2013.01); *G06N 20/10* (2019.01)

(58) Field of Classification Search
CPC ....... A61N 5/1031; G06N 20/10; G06F 17/18
See application file for complete search history.

(56) References Cited

U.S. PATENT DOCUMENTS

| 7,027,557 B2 | 4/2006 | Llacer |
| 10,762,167 B2 * | 9/2020 | Hartman ................ A61N 5/103 |

OTHER PUBLICATIONS

Appenzoller et al., "Predicting dose-volume histograms for organs-at-risk in IMRT planning", Nov. 27, 2012, Med. Phys. 39 (12), pp. 7446-7461. (Year: 2012).*

* cited by examiner

*Primary Examiner* — Ying Yu Chen
(74) *Attorney, Agent, or Firm* — LUMEN PATENT FIRM

(57) ABSTRACT

A treatment planning prediction method to predict a Dose-Volume Histogram (DVH) or Dose Distribution (DD) for patient data using a machine-learning computer framework is provided with the key inclusion of a Planning Target Volume (PTV) only treatment plan in the framework. A dosimetric parameter is used as an additional parameter to the framework and which is obtained from a prediction of the PTV-only treatment plan. The method outputs a Dose-Volume Histogram and/or a Dose Distribution for the patient including the prediction of the PTV-only treatment plan. The method alleviates the complicated process of quantifying anatomical features and harnesses directly the inherent correlation between the PTV-only plan and the clinical plan in the dose domain. The method provides a more robust and efficient solution to the important DVHs prediction problem in treatment planning and plan quality assurance.

1 Claim, 2 Drawing Sheets

DOSIMETRIC FEATURES-DRIVEN MACHINE LEARNING MODEL FOR DVHS/DOSE PREDICTION

CROSS-REFERENCE TO RELATED APPLICATIONS

This application claims priority from U.S. Provisional Patent Application Ser. No. 62/772802 filed Nov. 29, 2018, which is incorporated herein by reference.

STATEMENT OF GOVERNMENT SPONSORED SUPPORT

This invention was made with Government support under contract CA176553 awarded by the National Institutes of Health. The Government has certain rights in the invention.

FIELD OF THE INVENTION

This invention relates to dose-volume histograms (DHVs)/Dose prediction methods using a dosimetric feature-driven machine learning model approach.

BACKGROUND OF THE INVENTION

The development of intensity modulated radiation therapy (IMRT) and volumetric modulated arc therapy (VMAT) provides us with remarkable ability to maximize radiation dose to the planning target volume (PTV) while sparing for the critical organ-at-risks (OARs).

In the IMRT and VMAT workflow, the design of a patient-specific treatment planning is a critical step. Unfortunately, the planning process routinely used in the clinic remains time-consuming and labor-intensive, involving multiple manual trial-and-errors to obtain a clinically acceptable plan. Prior knowledge-based planning (KBP) has been studied to automate the plan selection process or to predict achievable plan/optimization parameters such as the dose-volume histograms (DVHs) of the OARs for a new case through machine learning algorithms or searching population-based plan libraries.

An accurate prediction of achievable DVHs on a patient-specific basis would greatly improve IMRT/VMAT planning in both efficiency and quality. An essence in establishing a predictive model is the choice of model input parameters correlative to the final treatment plan. Up to now, the predictive models rely heavily on the use of geometric and anatomical features of the OARs and target volumes. In these models, the efforts have been devoted to correlating the DVHs of OARs of the resultant plans to specific geometric or anatomical features.

Geometric/anatomical features play important roles in the construction of prediction models, and existing KBP-based methods have demonstrated the effectiveness of using geometric/anatomic features for DVH prediction. However, the strategy has pitfalls. While it is generally true that the resultant DVHs depend on the anatomy, the number of anatomical features that influence OAR dose sparing is rather large and may not be sufficient in establishing a reliable predictive model, especially in the presence of tissue density heterogeneities. In reality, the inter-patient variations of these anatomical features and their impact on the resultant OAR doses are very complicated. Given the complexity of the dose or DVH prediction problem at hand, it may become an intractable task to find an array of well quantified anatomical features to accurately predict achievable dose sparing for each OAR. In addition, few features characterizing the patients' dosimetric properties have been used in the existing prediction models, and merely using geometric/anatomical features to construct a prediction model may lead to suboptimal prediction.

In the present invention, instead of using the geometric/anatomical features or the features from the clinical treatment plan (CTP) of the patient, the inventors sought for additional relevant properties that are not part of the input data, but may be more descriptive of the final solution for the patient.

SUMMARY OF THE INVENTION

The present invention provides a treatment planning prediction method to predict a Dose-Volume Histogram (DVH) or Dose Distribution (DD) for patient data using a machine-learning computer framework. Key to this method is the inclusion of a Planning Target Volume (PTV) only treatment plan in the machine-learning computer framework. Dosimetric plan/parameters is/are used as an additional input to the machine-learning computer framework. This dosimetric input can also be considered as a set of parameters extracted automatically by a deep learning algorithm from the PTV-only treatment plan, which is defined as a treatment plan where an achievable dose distribution is achieved in absence of Organ-At-Risks (OARs) constraints. The method outputs a Dose-Volume Histogram and/or a Dose Distribution for the patient including the prediction of the dosimetric input parameter of the PTV-only treatment plan.

In another embodiment, the present invention provides a machine learning-based treatment planning prediction method that uses patient geometry information in the prediction method. Patient geometry information is defined as a relative position of a tumor, a relative position of a sensitive structure, or a combination thereof. In this embodiment, that method is improved by including a Planning Target Volume (PTV)-only treatment plan in the machine-learning computer framework. The machine-learning computer framework predicts a Dose-Volume Histogram (DVH) or a Dose Distribution (DD) for patient data. Input to the machine-learning computer framework is a dosimetric parameter as an additional input parameter. This dosimetric input parameter is a parameter obtained from a prediction of the PTV-only treatment plan, which is defined as a treatment plan where an achievable dose distribution is achieved in absence of Organ-At-Risks (OARs) constraints. The method outputs a Dose-Volume Histogram and/or a Dose Distribution for the patient including the prediction of the dosimetric input parameter of the PTV-only treatment plan.

In an alternate embodiment, a plan generated for the purpose of measuring the system's dosimetric ability or predicting the achievable dose plan on a patient specific basis could be provided or utilized by the framework as additional input parameters.

Compared with current geometric/anatomical feature-based approaches, the method of this invention alleviates the complicated process of quantifying anatomical features and harnesses directly the inherent correlation between the PTV-only plan and the clinical plan in the dose domain. By leveraging the high level dosimetric correlation, the invented method better models the system and provides a more robust and efficient solution to the important DVHs prediction problem in treatment planning and plan quality assurance.

Embodiments of the invention can be applied in the following manner:

Dosimetric features-driven machine learning model provides a simple yet accurate DVHs/dose prediction. The predicted DVHs/dose can be used as the objectives in knowledge-based planning and automated planning under the guidance of prior data.

The DVHs/dose distribution predicted from the model can also be used to evaluate treatment plans to ensure a high plan quality.

The use of dosimetric capability-based features in (simple) plans to correlate the dosimetric features (DVHs/dose distribution) of optimal plans in dosimetric domain.

Characterization of a priori plan or prior knowledge (e.g., for machine learning-based planning) and use them to guide the plan search in plan optimization algorithm or in deep learning model or in reinforcement learning model.

Use of the approach for automated treatment planning and treatment plan quality assurance.

The invention can be embodied as a method, a computer-implemented method executable and interpretable by a computer, or as a system where the method is integrated in a comprehensive system for dose prediction.

DETAILED DESCRIPTION

Figure 1:
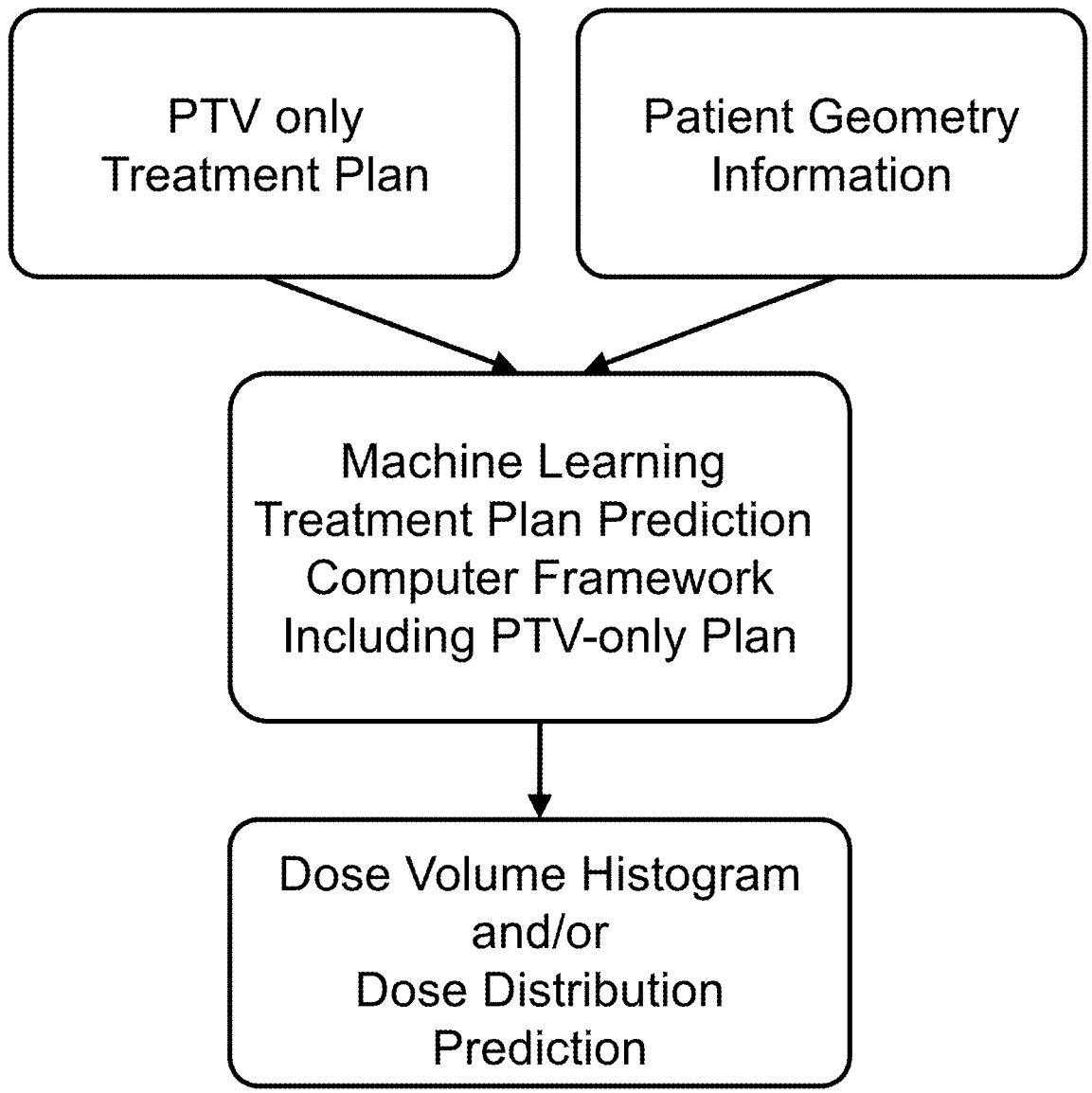
FIG. 1 shows a treatment planning prediction method including a PTV-only plan according to an exemplary embodiment of the invention.

The holy grail in dealing with the issue of DVH prediction is to find the most descriptive features of the system. For the prediction of best achievable DVHs for a given patient, there are obviously many types of input properties that may influence the resultant treatment plan. In general, the input parameters should be uniquely descriptive of the resultant plan, straightforward to obtain, and easily extendable to all disease sites. Instead of using the geometric/anatomical features or the features from the clinical treatment plan (CTP) of the patient, the objective in this invention was to seek additional relevant properties that are not part of the input data, but may be more descriptive of the final solution for the patient. To that objective, the inventors examined the feasibility of using the inherent capability (or the inherent likelihood) for the given case to meet the dosimetric goals as the input features and establish a machine-learning predictive model.

For a given RT modality and beam configuration, the differential dosimetric capability represents a priori knowledge of the system once the patient is chosen, and a detailed description on how to quantify intra-patient dosimetric capability and how to integrate the data into the inverse planning process was presented in a paper by the Lab of the inventors of this inventors (Shou et al. Quantitation of the a priori dosimetric capabilities of spatial points in inverse planning and its significant implication in defining IMRT solution space. Phys med biol. 2005; 50(7): 1469-1482).

While it is possible to aggregate voxel dosimetric capability to quantitatively describe intra-patient variation of the capability, in this invention, the inventors propose to measure the dosimetric capability by relying on the PTV-only VMAT plan, which provides the best scenario of targeting the tumor and worst scenario of sparing for OARs, i.e., the achievable dose distribution in the absence of OARs constraints.

The logic behind this method is that the difference in achievable OAR DVHs in the PTV-only plans for different patients reflects the oar geometric/anatomical difference. The DVHs of PTV-only plans not only explicitly provide dosimetric features, but also implicitly encode the inherent information related to geometric/anatomical features. A PTV-only plan is a strong indicator of what would be achievable in the final plan optimization and can serve as an input feature for the machine learning predictive model. The rationale is that, if it is far away from the clinical goals, the case is a "tough" one and it would be difficult to generate a plan that meets all clinical constraints.

To this extent, the purpose of this invention is to formally establish such a dosimetric capability-based machine learning approach for reliable prediction of the achievable DVHs of OARs. In this framework, the best achievable OAR DVHs are derived based on the input information of the DVHs from the PTV-only plans. Compared with current geometric/anatomical feature-based approaches, the invented method alleviates the complicated process of quantifying anatomical features and harnesses directly the inherent correlation between the PTV-only plan and the clinical plan in the dose domain. By leveraging the high level dosimetric correlation, the proposed approach promises. To better model the system and provide a more robust and efficient solution to the important DVH prediction problem in treatment planning and plan quality assurance (QA).

Prediction Pipeline

Figure 2:
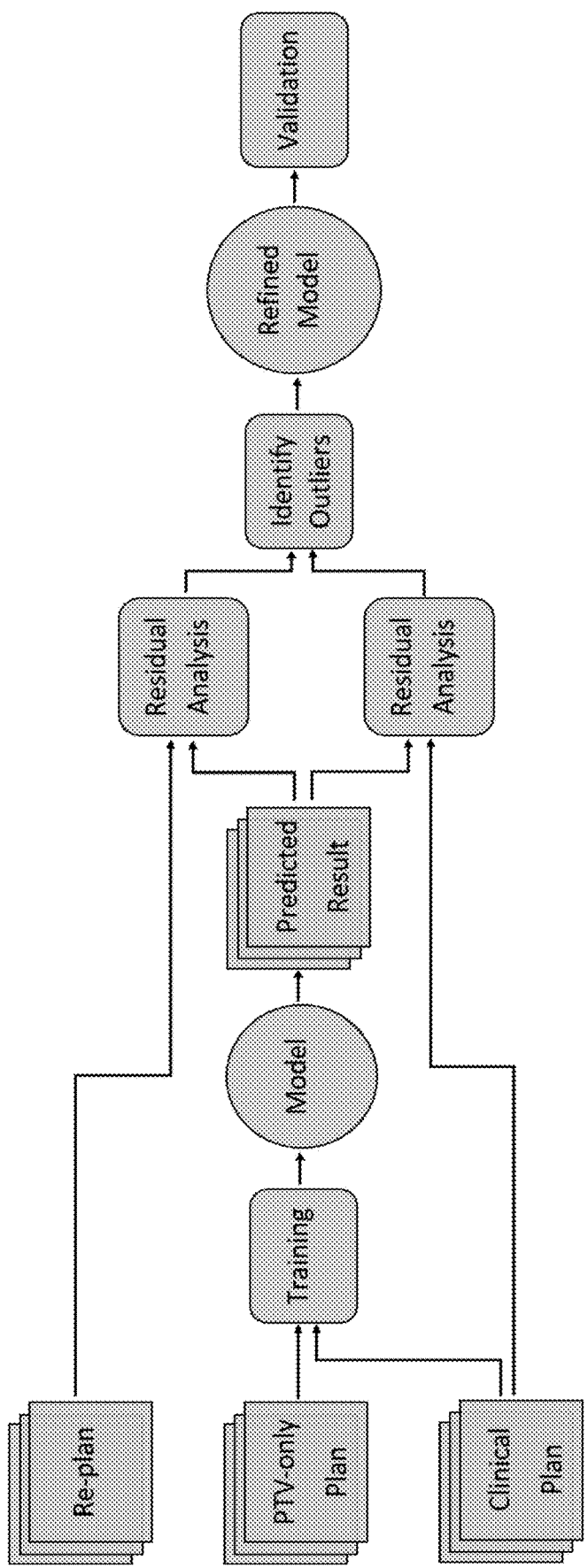
FIG. 2 shows a pipeline according to an exemplary embodiment of the invention.

To study the objective in this invention, two tasks were defined: (1) prediction model construction and (2) model validation. An overview of the pipeline is shown in FIG. 2. First the inventors leveraged the high-level correlation between the DVHs of the PTV-only plan and the corresponding clinical treatment plan and develop a robust predictive model. The input for training such a prediction model includes a database of prior clinical plans and the corresponding PTV-only plans. After training, a series of validation tests are performed.

Plan Database and RapidPlan Model Configuration

For the purposes of this invention, the inventors compared the invented prediction model with the RapidPlan model, which is a knowledge-based treatment planning tool available in Varian Eclipse treatment planning system (Varian Medical Systems, Palo Alto, Calif.) for DVH prediction of OARs to facilitate IMRT and VMAT treatment planning. The RapidPlan model is built based on the geometric/anatomical features including the distance-to-target histogram, OAR volume, target volume, overlapping volume, out-of-field volume, etc. In contrast, the prediction model of this invention is constructed using the dosimetric features. Both the invented prediction model and Rapid Plan model were trained on the same set of 53 prostate cancer plans. In addition, ten patients were randomly selected as an independent validation cohort. All these patients were treated between 2015 and 2018 by a single radiation oncologist following our institutional procedure and VMAT planning protocol using the Varian Eclipse treatment planning system (TPS). All the plans utilized two coplanar arcs, and dose prescriptions for clinically treated plans were 80 Gy in 40 fractions. The prostate and 1.5 cm of proximal seminal vesicles were defined as clinical target volume (CTV). PTV was created with a margin of 5 mm posteriorly and 8 mm in all other directions to CTV. For clinical plans, OARs included rectum, bladder, femoral heads, anal canal, penile bulb, corporal bodies, and bowel. The rectum was delineated from sigmoid flexure to the bottom of ischial tuberosities.

Table I

Clinical treatment planning objectives for planning target volume (PTV), rectum and bladder.

| Structure | Planning objectives [a] |
|---|---|
| PTV | D95%[%] = 100 |
|  | Dmax[%] ≤110 |
| Rectum | D10cc[Gy] <72 |
|  | D17%[Gy] <65 |
|  | D35%[Gy] <40 |
| Bladder | D25%[Gy] <65 |
|  | D50%[Gy] <40 |

[a] Dxcc[Gy], Dxcc[%], Dx %[Gy], Dx %[%]: Dose [Gy or %] to Volume [cc or % of total volume].

The planning objectives for PTV, rectum and bladder are listed in Table I. Specifically, for the PTV, all the plans were normalized such that 95% of the PTV volume was covered by 100% of the prescription dose. In addition to dosimetric objectives specified in Table I, the following constraints needed to be met:
(1) the entirety of CTV+5 mm posterior margin volume should receive 100% of the prescription dose, and
(2) 50% isodose line (IDL) should transverse the half of anterior/posterior extent of the rectum to ensure adequate rectum sparing without sacrificing CTV coverage when considering daily anatomical variations of prostate and rectum.

In addition to the clinical plan, a simple PTV-only VMAT plan for each patient was generated, using the same beam settings in the clinical plan. In PTV-only treatment planning, the inventors focused on the PTV performance (PTV coverage, PTV dose homogeneity, dose conformity and dose drop-off outside the PTV) and ignored the requirements of all OARs by treating them as normal tissues and not giving them specific constraints. A normal tissue objective (NTO) was kept as the same as that in the clinical plan to ensure PTV dose conformity and dose drop-off outside the PTV. The PTV-only plan here represents the best PTV performance plan by releasing the constraints of the involved OARs. The resultant OAR DVHs in the PTV-only plans depend on the relative geometric relations among the PTV and OARs. A prediction model based on the correlation in between the DVHs of the PTV-only plans and those of the clinical treatment plans can be used to predict OAR DVHs for a new patient. The optimization of the PTV-only plan was performed in the Varian Eclipse TPS as follows. First, the beam settings and normal tissue constraints were configured to be identical to those in the clinical plan of the patient. The inventors then set the two PTV constraints, including an upper constraint of 82 Gy with a priority of 100 and a lower constraint of 80 Gy with the same priority. The NTO parameters in Eclipse were typically set as this: priority of 150, distance from target border of 0.2 cm, start dose of 100%, end dose of 65% and fall-off of 0.2. Note that the OAR constraints were not applied.

The predicted DVHs by the dose-based KBP method were compared with that predicted by the geometric/anatomical features-based RapidPlan model for the purpose of assessing the feasibility and effectiveness of the invented prediction model.

Prediction Model

The prediction model was built by using support vector regression (SVR) to correlate the DVHs of the PTV-only plan and the clinical treatment plan. As a counterpart of the support vector machine (SVM), SVR is used for regression problems. SVM/SVR are supervised learning models, which build a hyperplane to separate data belonging to different classes by solving a quadratic optimization problem to maximize the margin between hyperplane and training data. For data that are not linearly separable, a kernel function is introduced to project the data into a higher dimensional space such that the projected data becomes linearly separable. In this invention, SVR was selected from a number of existing machine learning methods as the backbone of the prediction model for its known robustness, accuracy, and computational efficiency. The SVR models could be used to construct the sub-models for predicting the dosimetric endpoints (DEs) of the DVH. In the DVH prediction setting, each sub-model is built for predicting one DE in the DVH. Suppose a sequence of DEs for a DVH is denoted by $\mathfrak{D}$ below:

$$\mathfrak{D} = \{V_{d_1}, V_{d_2}, \ldots, V_{d_m}\},$$

where $d_i$ denotes the dose and $V_d$ represents the volume. For a PTV-only plan, its DVH can be represented by a sequence of DEs:

$$\mathfrak{D}^{\mathcal{P}} = \{V_{d_1}^{\mathcal{P}}, V_{d_2}^{\mathcal{P}}, \ldots, V_{d_m}^{\mathcal{P}}\}.$$

Likewise, a DVH of the corresponding clinical plan can be denoted by the following sequence of DEs:

$$\mathfrak{D}^{\mathcal{C}} = \{V_{d_1}^{\mathcal{C}}, V_{d_2}^{\mathcal{C}}, \ldots, V_{d_m}^{\mathcal{C}}\}.$$

The sub-model for the prediction of the i-th $\mathfrak{D}$, of the DVH is represented by $\mathcal{M}_i$, and the training data learned for the sub-model $\mathcal{M}_i$ is represented as follows:

$$X_i = \{(v_{d_i}^{\mathcal{P}_1}, v_{d_i}^{\mathcal{C}_1}), (v_{d_i}^{\mathcal{P}_2}, v_{d_i}^{\mathcal{C}_2}), \ldots, (v_{d_i}^{\mathcal{P}_n}, v_{d_i}^{\mathcal{C}_n})\},$$

where $v_{d_i}^{\mathcal{P}_j}$ and $v_{d_i}^{\mathcal{C}_j}$ denote the i-th DE in the j-th DVH of the PTV-only plan and the i-th DE in the j-th DVH of the clinical plan, respectively. After each of sub-models are built, the final high-level DVH prediction model $\mathbb{M}$ is constructed by integrating the above sub-models:

$$\mathbb{M} = \mathcal{M}_1 \oplus \mathcal{M}_2 \oplus, \ldots, \oplus \mathcal{M}_m.$$

In such a way, the resultant high-level prediction model $\mathbb{M}$ is trained to model the correlation between the DVH in the PTV-only plan and the DVH in the clinical plan. Thus, for each OAR, a high-level prediction model is built for prediction of the OAR DVH.

Model Validation and Improvement of the Training Datasets

The accuracy of the prediction model is checked through the residual analysis. The difference between the predicted DVHs and CTP DVHs can be quantified by the sum of absolute residuals (SAR), as given below:

$$SAR(D) = \Sigma_{D=0}^{\infty} |DVH^{\mathcal{C}}(D) - DVH^{\mathcal{P}}(D)| \cdot \Delta D, \quad (1)$$

where D denotes the dose, $\Delta D$ represents the discrete dose bin, $DVH^{\mathcal{C}}$ and $DVH^{\mathcal{P}}$ denote the DVH of clinical plan and the predicted DVH, respectively.

To improve the prediction capability, the constructed prediction model can be refined. The refinement process includes: (1) identification of suboptimal plans; and (2) exclusion of the identified suboptimal plans from current training cohort. The restricted sum of residuals (RSR) is employed to identify the suboptimal plans. The RSR between the $DVH^{\mathcal{C}}$ and $DVH^{\mathcal{P}}$ is formulated as:

$$RSR(D) = \Sigma_{D=0}^{\infty} \varepsilon(D) \cdot \Delta D \quad (2)$$

where ε(D) is given as follows:

$$\varepsilon(D) = \begin{cases} DVH^C(D) - DVH^P(D), & \text{if } DVH^C(D) - DVH^P(D) > 0 \\ 0, & \text{if } DVH^C(D) - DVH^P(D) \le 0 \end{cases} \quad (3)$$

The potential suboptimal plan is identified when the RSR between $DVH^c$ and $DVH^p$ is large. In this invention, the RSR is considered to be large if the RSR is greater than the sum of the mean and standard deviation (i.e., $\overline{RSR}+\sigma$) for the RSR values in the dataset. To confirm that the plan with large RSR value is suboptimal, re-planning is carried out for those plans with large RSR values. Re-plans were generated by an experienced dosimetrist to examine if there is any space to improve in OARs sparing, while keeping similar PTV dose coverage and dose uniformity. Refinement of the plan was done when the above situation was found to be the case. During the process of re-planning, the predicted values were not provided to the dosimetrist for reference. The achievable DVH improvement after re-planning with respect to the original CTP is quantified by the following sum of absolute residuals ΔSAR:

$$\Delta SAR = \Sigma_{D=0}^{\infty} | DVH^C(D) - DVH^R(D) | \cdot D, \quad (4)$$

where $DVH^R(D)$ denotes the DVH of the re-plan. The identified suboptimal CTPs are excluded from current training cohort, and the corresponding re-plans serve as the surrogates. The updated cohort of plans are used for learning a refined prediction model.

Results

The results discussed infra are with reference to the Figures and Tables included in U.S. Provisional Patent Application Ser. No. 62/772802 filed Nov. 29, 2018, which is incorporated herein by reference and to which this application claims the benefit of priority. Specifically, the results are discussed with reference to the Figures and Tables shown in Appendix A of U.S. Provisional Patent Application Ser. No. 62/772802.

As shown in FIG. 2 of Appendix A, the dose distributions and bladder and rectum DVHs of CTPs and PTV-only plans for two example cases from the training database. As can be seen, the DVH differences between the two plans are case-dependent and their values depend on the complicated geometrical relationship between PTV and the OARs, such as overlapping volume of the PTV and OAR, distance to PTV, PTV and OAR volume.

The prediction model was evaluated via residual analysis. Statistical analysis for the training cohort yielded the mean and standard deviation of SAR 0.023±0.011 for bladder and 0.044±0.020 for rectum, indicating the strong correlative relationship between the DVHs of the PTV-only plans and those of the CTPs. FIG. 3 of Appendix A compares the dosimetric endpoints, i.e., $V_{18}$, $V_{30}$, $V_{60}$, $V_{80}$ and $D_{mean}$ for the bladder, and $V_{15}$, $V_{45}$, $V_{65}$, $V_{80}$ and $D_{mean}$ for the rectum between the predicted DVHs and the CTP DVHs for the training cohort.

Dosimetric endpoints checks indicated that 52 out of 53 plans (98%) were within 10% error bound for bladder, and 45 out of 53 plans (85%) were within 10% error bound for rectum.

FIG. 3 of Appendix A compares the dosimetric endpoints between the predicted DVHs and the CTP DVHs for the 10 validation cases. The results demonstrated that for most cases the DE values in the predicted DVHs were close to those in the CTP DVHs for both bladder and rectum. Noteworthily, 92% and 96% of the points were within the 10% error bounds, which correspond to 10% OAR volume of the bladder and rectum. It was found that the DE values in 8 out of 10 validation plans (80%) were completely within 10% error bound for both bladder and rectum.

In FIGS. 5 and 6 of Appendix A, the predicted DVHs were compared with those predicted by RapidPlan and the CTP DVHs for the 10 validation cases. The CTP DVHs, RapidPlan and the prediction according to the method of this invention are represented by the orange, green and blue curves, respectively. As shown in FIG. 5 of Appendix A, the predicted DVHs of invented method for the bladder are closer to the CTP DVHs than those of RapidPlan for most cases. Likewise, for the rectum, the invented prediction model generated the DVHs, which are closer to the CTP DVHs than those of the RapidPlan on 10 validation cases for almost all of the cases, as shown in FIG. 6 of Appendix A.

Table II of Appendix A shows the results of residual analysis for ten validation cases. The bladder model in the invented method achieved the mean and standard deviation of SAR 0.034±0.028, as compared with 0.038±0.014 by the RapidPlan. The rectum model in the invented method obtained the mean and standard deviation of SAR 0.046±0.021 in contrast to 0.078±0.039 by the RapidPlan. This shows the effectiveness and better performance of the invented method in predicting the achievable DVHs. The average dose of the CTP was also computed, RapidPlan and the predicted DVHs according to the invented method for each validation case. The mean differences in the average dose between CTP and the inventors' prediction for bladder and rectum were 2.4 Gy and 2.0 Gy, respectively, as compared to 3.1 Gy and 9.6 Gy, respectively, between the CTP and RapidPlan. These results demonstrated that the average doses in the predicted DVHs according to this invention are closer to the CTP DVHs than that of the RapidPlan prediction.

Based on the analysis of the RSR values, two plans were identified as suboptimal with large RSR values. The first case has the RSR of 0.083 in the rectum, and the second case has the RSR of 0.154 in the rectum. The re-planning for the two cases were then done. FIG. 7 of Appendix A shows the comparison of dose distributions and DVHs between the original plans and revised plans for the two cases. As shown, significant improvement in rectum and bladder sparing were achieved with the re-planning. Table III of Appendix A compares the DEs for the original plans and re-plans on the two cases. Experimental results showed that the mean doses of the bladder and rectum in the first case are decreased from 19.0 Gy to 15.7 Gy, and from 41.3 Gy to 32.5 Gy, respectively. Likewise, for the second case, the mean doses of the bladder and rectum are decreased from 30.5 Gy to 28.9 Gy, and from 50.5 Gy to 42.3 Gy, respectively. The analysis of sum of residuals ΔSAR was done to quantify the DVH improvements for these two cases. The result showed that, for the first case, ΔSAR is 0.036 for the bladder and ΔSAR is 0.096 for the rectum, and for the second case ΔSAR is 0.018 for the bladder and ΔSAR is 0.091 for the rectum, indicating that the sparing of the bladder and rectum was improved.

Comments

While the output of a DVH predictive model is dosimetric, up to this point, few features characterizing the patients' dosimetric properties have been included in the model input. Indeed, past studies have tacitly ignored the dosimetric properties of the patient and focused on using geometric/anatomical features to construct a correlative model, which may lead to suboptimal prediction due to the intractable and even incomplete dependence of the patient's treatment plan on the selected features. In this invention, the inventors proposed to use the PTV-only plan as a metric to measure the potential for a patient's treatment plan to meet the dosimetric goals and established a machine learning prediction model based on the correlation between the PTV-only plan and the actual clinical treatment plan for a cohort of patients. Different from these existing knowledge-based planning methods, the technique of this invention takes the inherent dosimetric capability property of the patient into consideration and provides a conceptually intuitive and computationally straightforward approach. It should be emphasized that, although DVHs from PTV-only plans are used as the model input in this invention, DVHs or other dosimetric features from other different plans, such as OARs sparing-oriented plans, can also be used as the model input to build up the correlation model.

It is useful to emphasize here that in this invention the inventors are not using the features contained in the images or isodose plan to build their predictive model. Instead, the input is related to the potential for the planner to come up with a good plan and to meet the clinical dose-volume constraints. In reality, how to quantify the inherent capability or the likelihood for the OARs to meet their dosimetric goals and utilize the information to facilitate inverse planning is not well understood. The formalism is applied to prostate cases to illustrate the technical details of the new predictive model. Our study indicates that the inherent correlation between DVHs from the PTV-only plan and clinical plan is a useful dosimetric feature in prior knowledge modelling and enables an accurate and efficient prediction for the achievable DVHs.

An accurate prediction of achievable DVHs is beneficial for the improvement of quality of treatment plans, as the predicted achievable DVHs can be used as the starting point for planning of the patient and provide the planner with important guidance in treatment planning. This invention demonstrated the effectiveness of the invented method in predicting achievable DVHs using ten randomly selected cases. In addition to facilitating the treatment planning process, the method can also serve as a quality control tool for treatment planning. The technique provides an effective mechanism to incorporate prior knowledge of the system into the IMRT/VMAT inverse optimization process and enables one to better model the intra-structural tradeoff. Compared with the conventional prediction techniques, the invented method relieves the computation burden of quantifying geometric/anatomical features and provides a more efficient solution to the DVH prediction problem in treatment planning and plan quality control by directly harnessing the high level dosimetric correlation.

What is claimed is:

1. A treatment planning prediction method, comprising:
  (a) training a machine deep learning algorithm operable by a computer wherein the machine deep learning algorithm is trained to correlate (i) Dose-Volume Histograms (DVHs) or Dose Distributions (DDs) from Planning Target Volume (PTV) only treatment plans with (ii) DVHs and DDs of treatment plans for patients, wherein the PTV only treatment plans are defined as treatment plans where dose constraints to Organs-At-Risk (OARs) have been removed and have PTV constrains defined for dose homogeneity and dose conformity;
  (b) the computer receiving dosimetric parameters, defined as DVHs or DDs from a PTV only treatment plan for a new patient, and the computer inputting the dosimetric parameters into the machine deep learning algorithm;
  (c) the computer processing the inputted dosimetric parameters by the machine deep learning algorithm; and
  (d) the computer generating an output from the machine deep learning algorithm, wherein the output are DVHs or DDs for the new patient, wherein the output is characterized by containing OARs constraints for the new patient as well as PTV constrains defined for dose homogeneity and dose conformity for the PTV only treatment plan for the new patient.

* * * * *